(12) United States Patent
Bonsignore

(10) Patent No.: US 8,133,268 B2
(45) Date of Patent: Mar. 13, 2012

(54) STENT/FIBER STRUCTURAL COMBINATIONS

(75) Inventor: Craig Bonsignore, Pleasanton, CA (US)

(73) Assignee: Cordis Corporation, Bridgewater, NJ (US)

( * ) Notice: Subject to any disclaimer, the term of this patent is extended or adjusted under 35 U.S.C. 154(b) by 275 days.

(21) Appl. No.: 11/755,171

(22) Filed: May 30, 2007

(65) Prior Publication Data

US 2008/0300668 A1 Dec. 4, 2008

(51) Int. Cl.
*A61F 2/06* (2006.01)

(52) U.S. Cl. ..................... 623/1.16

(58) Field of Classification Search .............. 623/1.15, 623/1.16, 1.17, 1.18, 1.2, 23.7, 1.13, 1.38, 623/1.47, 1.54
See application file for complete search history.

(56) References Cited

U.S. PATENT DOCUMENTS

| | | | | |
|---|---|---|---|---|
| 4,942,875 | A * | 7/1990 | Hlavacek et al. | 606/230 |
| 5,147,400 | A * | 9/1992 | Kaplan et al. | 623/13.18 |
| 5,500,013 | A * | 3/1996 | Buscemi et al. | 623/1.22 |
| 5,591,222 | A * | 1/1997 | Susawa et al. | 606/195 |
| 5,876,432 | A * | 3/1999 | Lau et al. | 623/1.13 |
| 6,565,599 | B1 * | 5/2003 | Hong et al. | 623/1.15 |
| 2002/0120327 | A1 * | 8/2002 | Cox et al. | 623/1.16 |
| 2003/0153972 | A1 * | 8/2003 | Helmus | 623/1.15 |
| 2003/0208260 | A1 | 11/2003 | Lau et al. | |
| 2004/0199241 | A1 * | 10/2004 | Gravett et al. | 623/1.13 |
| 2006/0009798 | A1 * | 1/2006 | Callister et al. | 606/200 |
| 2006/0173529 | A1 * | 8/2006 | Blank | 623/1.16 |

FOREIGN PATENT DOCUMENTS

| | | |
|---|---|---|
| EP | 1834606 A1 | 9/2007 |
| WO | WO 00/42947 A2 | 7/2000 |
| WO | WO 2006/083991 A2 | 8/2006 |
| WO | WO 2006/099450 A2 | 9/2006 |
| WO | WO 2006/127825 A1 | 11/2006 |

OTHER PUBLICATIONS

European Search Report dated Oct. 2, 2008 for corresponding EP Application No. EP08251858.

* cited by examiner

*Primary Examiner* — Ryan Severson
*Assistant Examiner* — Jonathan W Miles
(74) *Attorney, Agent, or Firm* — Dergosits & Noah LLP; Todd A. Noah

(57) ABSTRACT

A plurality of endoluminal segments axially connected by fiber bridges is disclosed. The endoluminal segments may either be balloon-expandable or self-expanding, with the preferred embodiment being superelastic nitinol. The intraluminal segments may possess a textured surface or at least one geometric feature per segment, preferably located at the apex of a strut pair comprising the intraluminal segment, preferably capable of serving as an anchoring point for the fiber bridges. These geometric features may transmit axially compressive loads during deployment from a device such as a catheter, and may further be capable of interlocking the endoluminal segments when constrained within a device such as a catheter. The fibers comprising the bridges may be polymeric, silk, collagen, bioabsorbable, or a blend thereof. The fiber network comprising the bridges may be regularly oriented, randomly oriented, localized, or continuous. Moreover, the intraluminal segments and fiber bridges may be individually impregnated with therapeutic material, or may both be impregnated with therapeutic material.

17 Claims, 7 Drawing Sheets

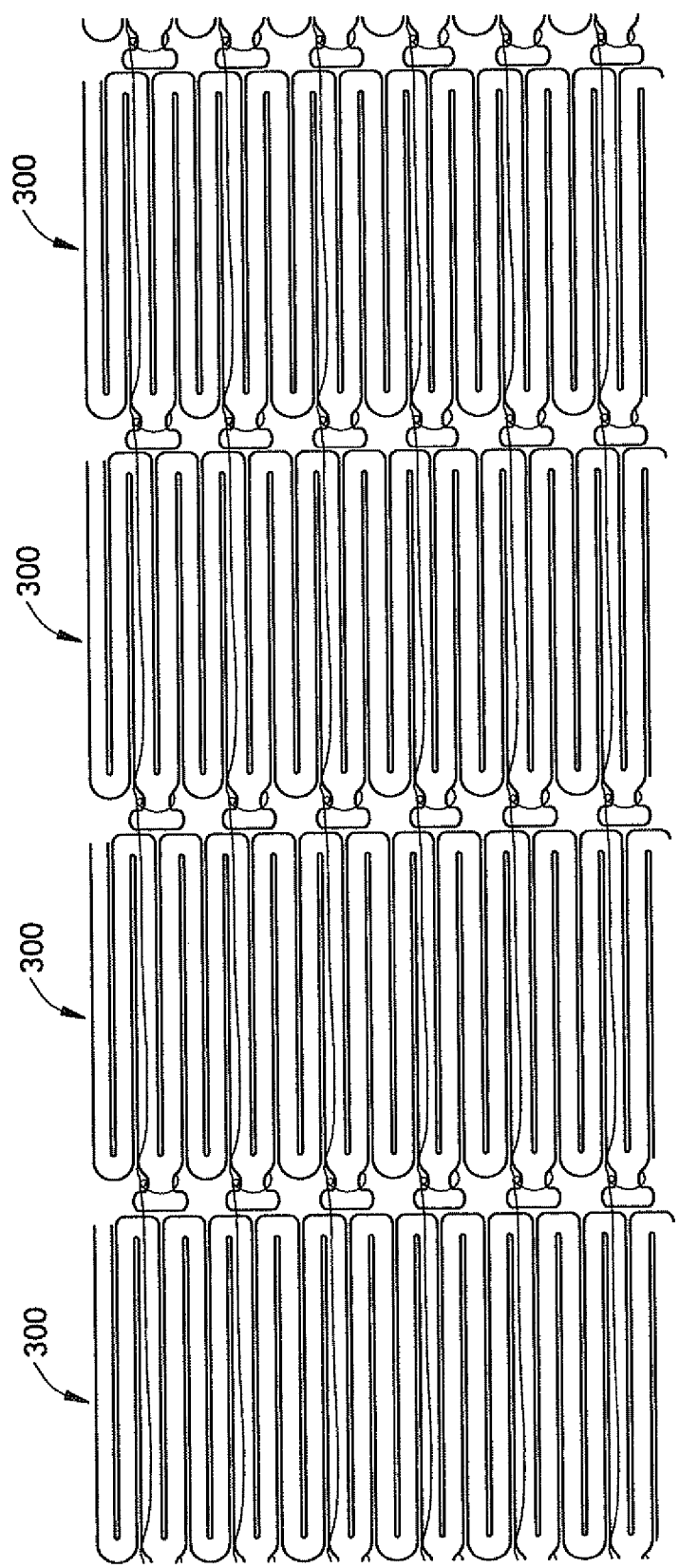

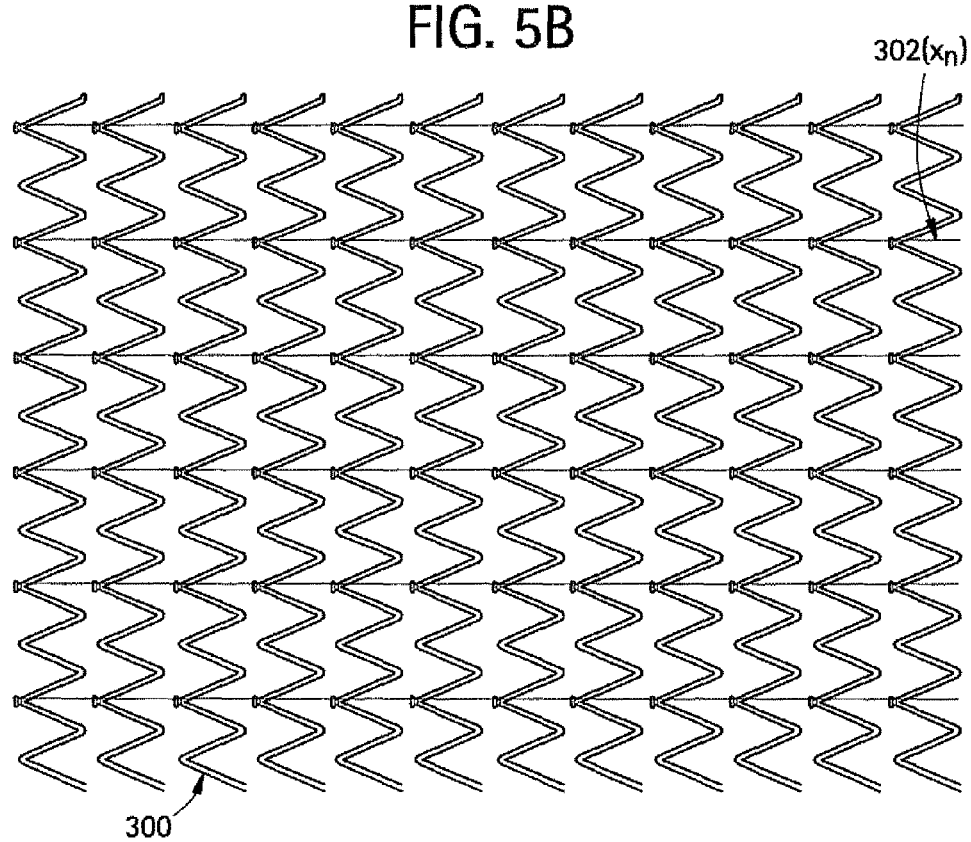

STENT/FIBER STRUCTURAL COMBINATIONS

BACKGROUND OF THE INVENTION

1. Field of the Invention

The present invention relates to axially connected intraluminal segments and more particularly to individually expandable segments connected at least partially by fibers. In addition, the present invention relates to intraluminal devices, and more particularly to intraluminal devices, such as stents, incorporating fibers that operate as bridges axially connecting adjacent stent segments. The present invention also relates to stent structures having geometric features that serve as fixation points for the fibers described herein.

2. Discussion of the Related Art

Intraluminal devices have been known in the art for a number of years. These devices have utilized a variety of materials, but commonly fall into two broad categories; namely, self-expanding and balloon-expandable. Nickel-titanium is a common material selected for use in self-expanding device designs, while stainless steel and cobalt alloys have been common materials in balloon-expandable devices.

The flexibility of these devices is an important factor affecting delivery and performance within the body of the patient. A tortuous vascular anatomy requires a device to be able to conform to the anatomical conditions, before and after deployment, while preserving the device's primary functionality. Self-expanding materials provide superior flexibility relative to balloon-expandable materials for the specific reason that the self-expanding materials tend to conform to a tortuous anatomy with less tissue trauma than balloon-expandable materials. Examples of self-expanding intraluminal devices include stents, vena cava filters, distal protection devices, and occluders. However, maximizing the flexibility of intraluminal devices may lead to negative tradeoffs in other aspects of the device's mechanical performance, such as radial strength and buckling resistance. Additionally, in many cardiovascular applications, the device may be subject to significant dynamic deformations such as twisting, axial extension/compression and bending not seen in other parts of the vasculature. Under such conditions, a device should preferably be able to tolerate large dynamic deformations while remaining intact such that its primary functionality is preserved.

Radially expandable intraluminal devices commonly comprise a plurality of axially adjacent radially expandable segments. Such axially adjacent radially expandable segments are often joined by connecting elements generally described as bridges. In some cases, these bridge elements are not radially deformable, but rather are axially deformable, allowing for relative motion between axially adjacent radially expandable segments. This relative motion may desirably accommodate static or dynamic bending, stretching, or compression of the implanted device. The number of bridge elements present around the circumference of a design is an important design consideration. Fewer bridge connections allow for more flexibility and conformability, but potentially compromise scaffolding uniformity and vessel coverage. More bridge connections improve scaffolding uniformity, but potentially result in an undesirably stiff structure.

Radially expandable intraluminal devices are commonly fabricated such that the radially expandable segments and bridge elements are integral, or formed from a single continuous material, and therefore the finished device is a single contiguous structure.

The above described loading cases of bending, flexion, stretching, and compression create design challenges for flexibility and durability of intraluminal implants. One solution to these design concerns is to provide a design with fewer integral bridging elements, or ultimately no integral bridging elements, such that each segment is subject to only the localized forces and deformations at its immediate location. This design presents some difficulty in the precise placement of the individual segments within the target area of the lumen. Specifically, in the instance of self-expanding materials, the device is introduced in a constrained state within a sheath. As the constraint is removed from the self-expanding segment, the rapid increase in diameter creates axially directed forces which would tend to propel the segment forward in the absence of adequate axial constraint between the expanding segment and axially adjacent constrained segment still completely or partially within the sheath. In circumstances where the segment length is somewhat short in comparison to its diameter, this may result in the segment jumping forward from the distal tip of the delivery device, which in turn creates difficulty in the precise placement of the segment. Additionally, there is a need to provide a means for ensuring the uniformity and stability of adjacent segments during deployment. Accurate placement of intraluminal devices is of paramount importance to ensure that problems such as inaccurate placement over target lesions, distortion, or occlusion of critical branch vasculature does not occur.

In addition, intraluminal devices are a known means for the delivery of therapeutic agents to localized areas within the body of the patient. A common method for combining the delivery of therapeutic agents into the performance of an intraluminal device involves coating the surface of the device with a polymer containing the therapeutic agent. The surface area of the device becomes a limiting factor in the quantity of therapeutic agents that may be delivered. Coating the device with a polymer may also present difficulty in controlling coating adhesion, controlling coating thickness, and controlling coating interaction with the therapeutic agent. Consequently, increasing the available surface area of the device without sacrificing its mechanical performance and flexibility, or eliminating the need for coating the device surface may simplify the manufacture and efficacy of such devices.

Accordingly, there exists a need for intraluminal devices that that avoid the problems described herein.

SUMMARY OF THE INVENTION

The present invention overcomes the disadvantages associated with current intraluminal implant designs as briefly described above.

In accordance with one aspect, the present invention is directed to an implantable intraluminal medical scaffold. The implantable scaffold comprises one or more radially expandable stent segments and one or more fiber bridges interconnecting the one or more radially expandable segments to form a substantially tubular structure.

Radially expandable intraluminal devices are commonly fabricated such that the radially expandable segments and bridge elements are integral, or formed from a single continuous material, and therefore the finished device is a single contiguous structure. The present invention is distinct in that some or all of the bridge elements may be comprised of a material separate and distinct from the material from which the radially expandable intraluminal device is fabricated. Preferably, the radially expandable intraluminal device structure is fabricated from metal, while the separate bridging elements are fabricated from a non-metallic polymer material. The present invention also describes means for joining the metallic and non-metallic or polymeric elements to provide a useful device assembly.

In one exemplary embodiment, the present invention is directed to a series of adjacent intraluminal segments at least partially interconnected with a network of fibers. The fibers supplement or replace conventional integral bridging elements that are contiguous with radially expandable segments. The fibers preferably allow the individual intraluminal segments to move with some degree of independence from one-another while providing the benefit of the flexible axial connection between segments. The fibers may be oriented randomly or regularly while preferably not inhibiting the expansion of the intraluminal segments to a diameter sufficient to maintain lumen patency and the ability of the intraluminal segments to be constrained to a reduced diameter.

In another exemplary embodiment, the present invention is directed toward individual intraluminal segments possessing a feature, or features, that provide a means for securing fibers to the individual intraluminal segments. An individual segment may possess one or more features to which the fibers may be attached. The features may be of any geometry that provides a means for securing fibers. Examples of contemplated feature geometries include micro features such as textured surfaces, and macro features such as eyelets, tabs, anvils, and the like. The features may also provide other functionality in combination with, or exclusive of, securing the fibers. Additional functionalities may include the interconnection of intraluminal elements prior to completed deployment. The fibers may be secured to the feature through any suitable means such as solvent bonding, looping, knotting, threading, and the like. The fibers may be oriented randomly or regularly while preferably not inhibiting the expansion of the intraluminal segments to a diameter sufficient to maintain lumen patency. Additionally, the fiber elements may be constructed as individual filaments, with ordered or random placement, or the fiber elements may be individual strands incorporated into larger fiber networks such as braids, weaves, threads, and the like. The fibers may form individual or localized patterns, or may form continuous patterns. The fiber elements may be of any composition suitable for implantation into the body of a living patient such as polymers, silk, collagen, bioabsorbable materials, and the like. The fibers preferably provide an improved means for accurate implant deployment, implant flexibility, and implant durability. Moreover, the some or all of the fibers may be used as a means for delivering therapeutic agents to the patient, either as the exclusive means, or as an additional means supplementing similar functionality, including the intraluminal segments and procedural method. Intraluminal segments may be any self-expanding or balloon-expandable material, or combination of both.

More specifically, the present invention is directed to a stent comprising adjacent radially expanding stent segments interconnected via a network of fibers or meshes. The present invention provides increased therapeutic versatility to stents of any architecture; further, it provides a means to enhance the axial stability and uniformity of stent architectures having conventional integral metallic bridges connecting axially adjacent radially expandable segments; further provides for a fiber connection of a series of short radially expandable stent segments which are otherwise unconnected. This design also provides for positioning the stents in an axial series with a predetermined gap between each segment.

The present invention provides axial integrity to a series of stents, such that the individual stent segments may not pull apart from each other when the structure is pulled into axial tension as described above.

The present invention provides integrity for a series of stents when in a constrained or expanded configuration. The present invention provides structural integrity until the stent structure is delivered and deployed in the target vessel. This axial integrity is particularly important at the moment during which the constrained stent segment emerges from the delivery system and immediately begins to expand. The force of this expansion would tend to propel the individual stent segments forward uncontrollably without the axial connection provided by the described fibrous connection.

The axial connection provided by the fiber is not necessarily needed after the implant has been delivered and deployed. As such, the fiber could be made from a bio-absorbable or dissolving material.

It is expected that the fiber will be combined with the stent structure when it is in its expanded configuration (typically 5-10 mm). The fiber should preferably not inhibit radial constraint of the stent from its expanded configuration to its low-profile delivery configuration (typically 1-2 mm).

For a device constructed of a self-expanding material such as nitinol, the fiber should preferably not inhibit radial expansion of the stent structure from its delivery configuration to its memory configuration when deployed at the time of implantation.

The nitinol structure may be constrained from its expanded configuration to its delivery configuration under conditions of extreme chilling (typically −10 to −60 degrees C.). Ideally, the fiber material would be able to withstand such chilling, and would maintain its ability to be constrained in diameter without inhibiting radial constraint of the stent structure.

The memory shape and mechanical characteristics of nitinol are programmed using a series carefully controlled thermal exposures at various temperatures that are known in the art. Ideally, the completed nitinol stent structure should not be exposed to elevated temperatures (greater than 60 degrees C.). Ideally, the fiber material would be able to withstand such temperatures, and would maintain its ability to be constrained in diameter without inhibiting radial constraint of the stent structure.

Preferably, the fiber material may also serve as a platform for delivery of drugs or related therapeutic agents as well as a structural element.

Preferably, the fiber should have proven biocompatibility as an implantable material, and should be commercially available for such purposes.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 5a is a schematic view of the exemplary embodiment illustrated in FIG. 3, wherein the intraluminal segments are at a compressed diameter in accordance with the present invention.

FIG. 5b is a schematic view of the exemplary embodiment illustrated in FIG. 3 wherein the intraluminal segments are at an expanded diameter in accordance with the present invention.

DETAILED DESCRIPTION OF THE PREFERRED EMBODIMENTS

The present invention is directed to a stent comprising individual segments interconnected by a mesh or fibers. These fibers are integrated with each other and the radially expandable stent segments in such a way that provides an axial bridge connection between the stent segments without inhibiting radial expansion or constraint of the stent segments.

Figure 1:
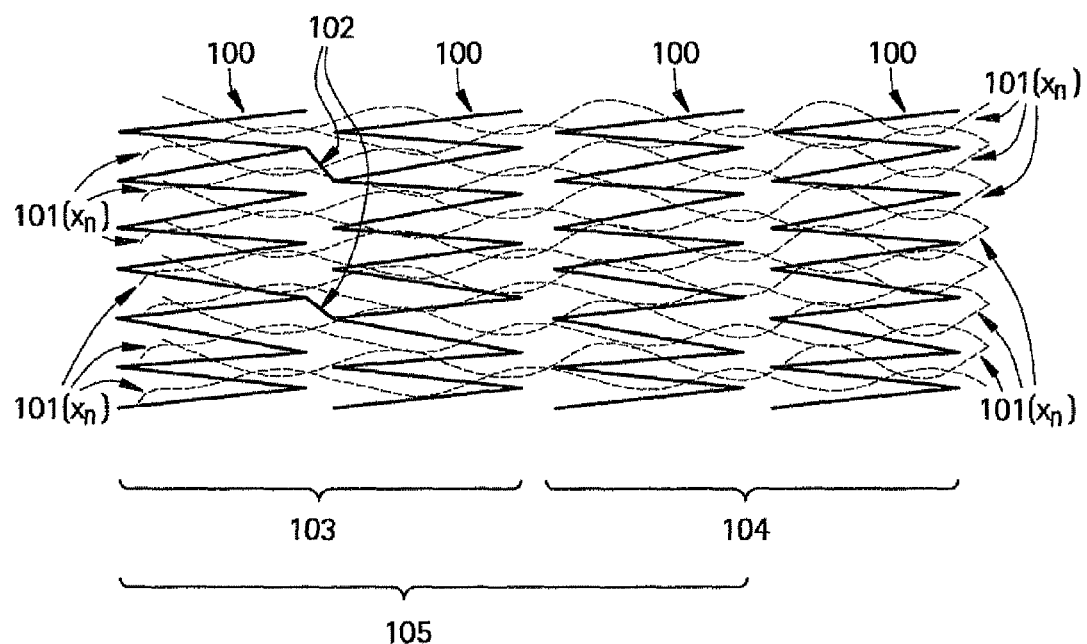
FIG. 1 is a schematic view of an exemplary stent-fiber combination wherein a network of fibers is intertwined with intraluminal segments in accordance with the present invention.
Figure 7:
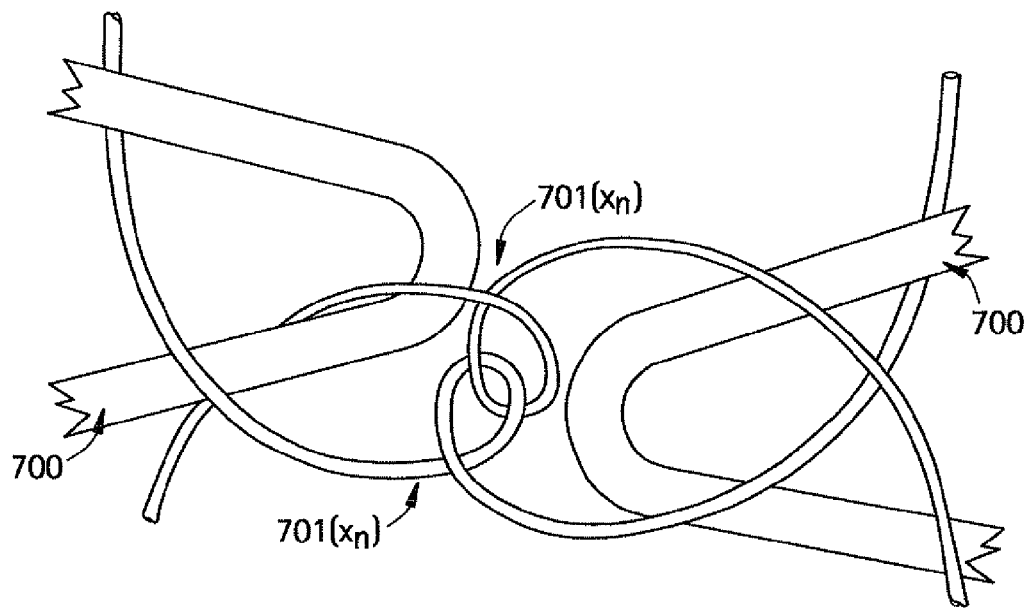
FIG. 7 is a detailed view of an alternate exemplary embodiment of the stent-fiber combination illustrated in FIG. 1 in accordance with the present invention.

FIG. 1 illustrates a plurality of adjacent intraluminal stent segments 100 axially connected by a network of fibers 101 ($x_n$) where "$x_n$" represents the number of fibers present, ranging from 1 to about $1 \times 10^9$. Each adjacent segment 100 is preferably self-expanding, but may also be balloon-expandable. Adjacent segments may be axially connected by integral bridging elements 102 as in the group of segments 103, may be axially independent as in the group of segments 104, or may be a combination of both as in the group of segments 105. Fibers 101 axially connect at least two adjacent segments 100. A preferred exemplary embodiment is a self-expanding intraluminal segment 100 made from a superelastic alloy such as nickel-titanium (nitinol) comprising from about 50.0 weight percent Ni to about 60 weight percent Ni, with the remainder being Ti. Preferably, each intraluminal segment 100 is designed such that it is superelastic at body temperature, having an austenitic finish temperature in the range from about twenty-two degrees Celsius to about thirty-seven degrees Celsius. Fibers 101($x_n$) are most preferably polymers, silk, collagen, or bioabsorbable compositions. In FIG. 1, fibers 101($x_n$) may be of one, or more than one material composition, including embodiments where single fibers 101 ($x_n$), or groups of fibers 101($x_n$) are composed of differing materials relative to the other fibers 101($x_n$) forming an interwoven network. Fibers 101($x_n$) may be oriented randomly, or in a regular pattern, such that the fibers 101($x_n$) preferably allow the intraluminal segments 100 to move relative to one another while axially connected through the network of fibers 101($x_n$). One preferable means for allowing relative movement is illustrated in FIG. 7, where fibers 701($x_n$) are looped over one another while being passed over and under the struts forming the individual intraluminal segments 700.

Figure 2:
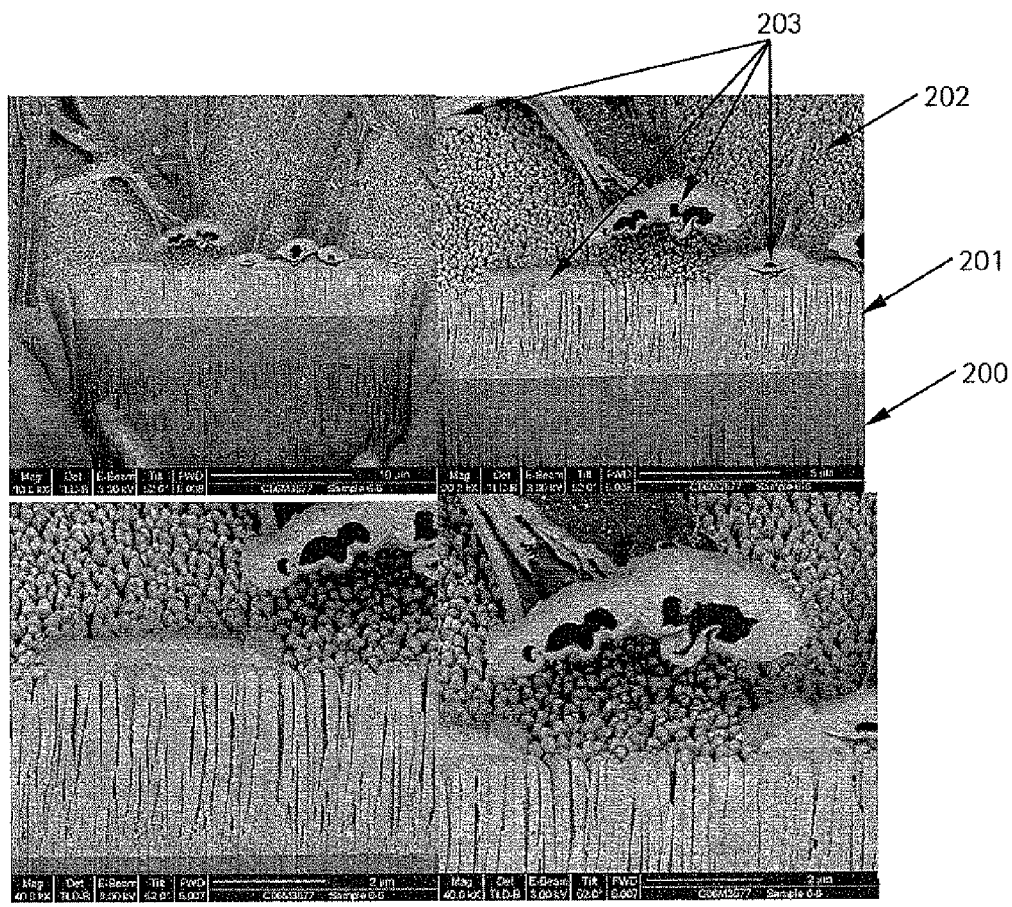
FIG. 2 is a series of photographs of a preferred embodiment of FIG. 1 wherein a textured metallic surface provides improved adhesion between the fibers and metallic substrate.

FIG. 2 illustrates a preferred embodiment of a textured surface designed to optimize the adhesion of polymer fibers to a metallic radially expandable intraluminal implant. This highly magnified view illustrates a metallic coating 201 with a textured surface 202 deposited on a substrate 200. The textured surface 202 provides increased surface area to improve bonding of polymeric fibers 203. In a preferred embodiment, the metallic coating 201 provides a biocompatible surface and is securely bound to the base metallic structure 200 using a physical vapor deposition process. In a preferred embodiment, metallic coating 201 is tantalum and the substrate 200 is a radially expandable metallic nitinol segment. Tantalum has the benefits of enhancing radiopacity, as well a preserving biocompatibility of the device. The polymer fibers 203 are joined to metallic surface 202 with the aid of a solvent which allows at least some of the dissolved polymer to form an interface between the textured surface and fiber.

Figure 3:
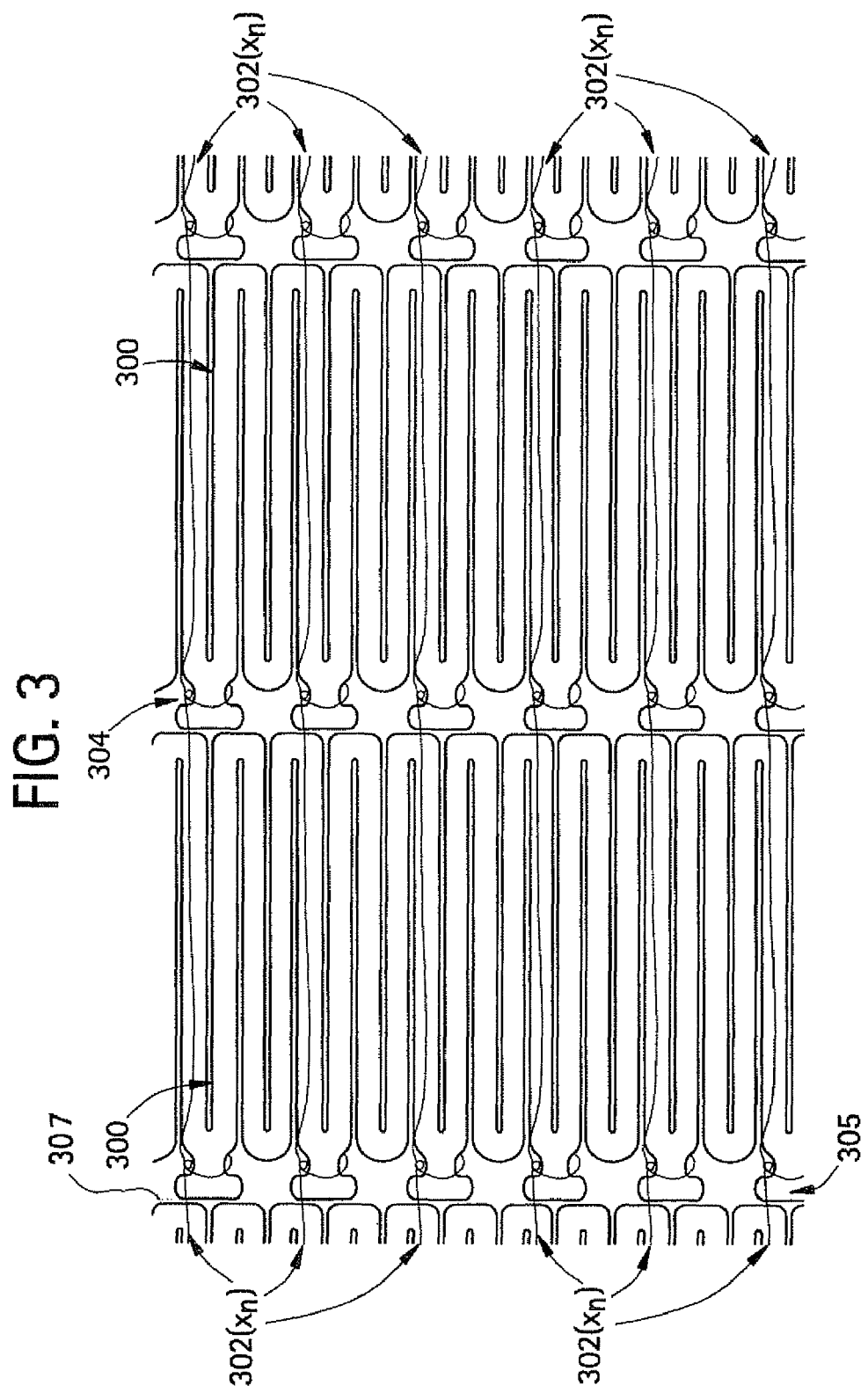
FIG. 3 is an alternate exemplary embodiment of FIG. 1 wherein fibers are attached to anchoring features on the intraluminal segments in accordance with the present invention.
Figure 4:
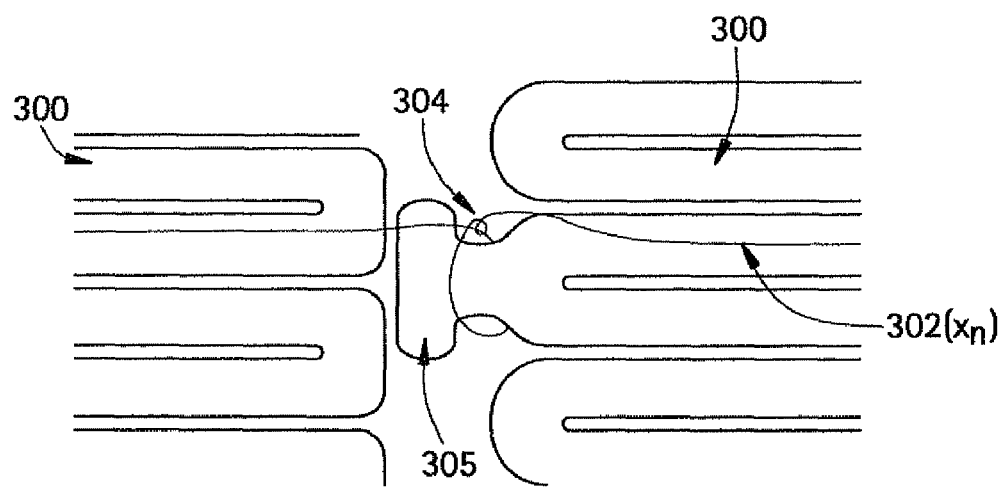
FIG. 4 is an enlarged detail view of the exemplary embodiment illustrated in FIG. 3.

In accordance with another exemplary embodiment, FIG. 3 and FIG. 4 illustrate a plurality of intraluminal segments 300 connected by a plurality of fibers 302($x_n$), where "$x_n$" represents the number of fibers present, ranging from 1 to about $1 \times 10^9$. The intraluminal segments 300, and fibers 302($x_n$) are substantially as described in FIG. 1, where intraluminal segment 300 has at least one additional geometric feature 305, such as a notched tab having a flat bearing surface, preferably located at the apex of an individual strut pair comprising the intraluminal segment 300 structure. The geometric feature 305 serves as an attachment point between fibers 302($x_n$) and intraluminal segments 300. The geometric feature 305 or notched tab may further serve to provide a means for transmitting axially compressive loads between intraluminal segments 300 during deployment within the target lumen. The geometric features 305 contacts the flat bearing surface 307 formed by the strut pairs. In addition, the geometric feature 305 may comprise a material that is more radiopaque than the remaining portions of the structure, thereby serving as a marker for accurate deployment of the device. As illustrated in FIG. 3 and FIG. 4, one preferred means for attaching the fiber 302($x_n$) to the geometric feature 305 of the intraluminal segment 300 is to create a knotted loop 304. The fibers 302($x_n$) that form a network connecting intraluminal segments 300 may be of a single material composition such as those mentioned as being preferable in FIG. 1, or may be of more than one preferable material.

FIG. 5a and FIG. 5b are schematic representations of the exemplary embodiment illustrated in FIG. 3 and FIG. 4 and described herein. FIG. 4a shows a plurality of intraluminal segments 300, having geometric features 305 and connected fibers 302($x_n$) that are radially compressed in a manner generally consistent with being constrained within a catheter. FIG. 5b shows the same plurality of intraluminal segments 300, geometric features 305, and connected fibers 302($x_n$) and 304 as in FIG. 5a, however, the intraluminal segments 300 are in the fully-expanded state.

In accordance with another alternate exemplary embodiment, intraluminal segments 100 connected by a network of fibers 101($x_n$) as shown in FIG. 1, or a network of fibers 302($x_n$) as shown in FIG. 3 through FIG. 5b, are a means for delivering therapeutic agents to the patient. A detailed description of exemplary agents is included herein. The fibers 301($x_n$) or 302($x_n$) may either be the exclusive means of delivery, or may provide surface area in addition to that of the intraluminal segments 100, 300. Fibers 101($x_n$) or 302($x_n$) are most preferably impregnated with therapeutic agents, or combinations of therapeutic agents, such as those that inhibit the formation of thrombus, or the reoccurrence of stenosis. The fibers 101($x_n$) or 302($x_n$) that form a network connecting intraluminal segments 100, 300 may be of a single material composition such as those mentioned as being preferable in FIG. 1, or may be of more than one preferable material thereby creating a blended fiber.

Figure 6:
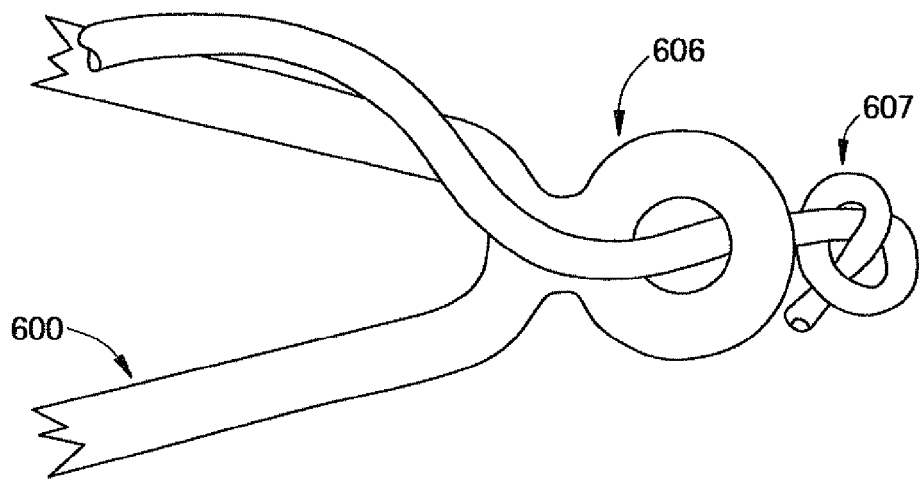
FIG. 6 is a detailed view of an alternate exemplary embodiment of the stent-fiber combination illustrated in FIG. 3 in accordance with the present invention.

In accordance with yet another exemplary embodiment, FIG. 6 illustrates the detail of a geometric feature 606 similar to the feature 305 shown in FIG. 3 and FIG. 4. In this exemplary embodiment, the geometric feature 606 is substantially similar to that of 305 in that it serves as an anchoring point for a fiber 607, or fibers 607, as well as providing a means for transmitting axially compressive forces between intraluminal segments 600 during deployment to the target lumen. In this exemplary embodiment, the fiber 607 is passed through the eyelet preferably formed by the geometric feature 606, where the fiber 607 terminates in a manner, such as a knot that preferably restrains the terminus of the fiber 607 from falling out of the geometric feature 606. The means by which fibers 607 are secured to the plurality of intraluminal segments 600 may either be through knotting the fiber 607 at its termination points on the first (proximal) and last (distal) intraluminal segments 600, or at intervals between intraluminal segments 600 along the length of the fiber 607. The geometric feature 606 is preferably located at the apex formed by adjacent struts comprising intraluminal segment 600, where there is preferably at least one feature 606 on each intraluminal segment 600 present. The fibers 607 that form a network connecting intraluminal segments 600 may be of a single material composition such as those mentioned as being preferable in FIG. 1, or may be of more than one preferable material. The number of fibers 607 present may range from 1 to about $1 \times 10^9$. Optionally, the fibers 607 may either be the exclusive means, or may provide surface area in addition to that of the intraluminal segments 600, for the delivery of therapeutic agents. Fibers 607 are most preferably impregnated with therapeutic agents, or combinations of therapeutic agents, such as those that inhibit the formation of thrombus, or the reoccurrence of stenosis.

It is important to note that the fibers may incorporate any suitable biocompatible materials that may be non-absorbable or absorbable depending upon the application.

As set forth above, the stent segments, the fibers or both may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagines); antiplatelet agents such as G(GP) $ll_b/lll_a$ inhibitors and vitronectin receptor antagonists; anti-proliferative/anti-mitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine and cytarabine) purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory; such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalec), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors, antisense oligionucleotides and combinations thereof, cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

In accordance with another exemplary embodiment, the stents described herein, whether constructed from metals or polymers, may be utilized as therapeutic agent or drug delivery devices. The metallic stents may be coated with a biostable or bioabsorbable polymer or combinations thereof with the therapeutic agents incorporated therein. Typical material properties for coatings include flexibility, ductility, tackiness, durability, adhesion and cohesion. Biostable and bioabsorbable polymers that exhibit these desired properties include methacrylates, polyurethanes, silicones, polyvinylacetates, polyvinylalcohol, ethylenevinylalcohol, polyvinylidene fluoride, poly-lactic acid, poly-glycolic acid, polycaprolactone, polytrimethylene carbonate, polydioxanone, polyorthoester, polyanhydrides, polyphosphoester, polyaminoacids as well as their copolymers and blends thereof.

In addition to the incorporation of therapeutic agents, the coatings may also include other additives such as radiopaque constituents, chemical stabilizers for both the coating and/or the therapeutic agent, radioactive agents, tracing agents such as radioisotopes such as tritium (i.e. heavy water) and ferromagnetic particles, and mechanical modifiers such as ceramic microspheres. Alternatively, entrapped gaps may be created between the surface of the device and the coating and/or within the coating itself. Examples of these gaps include air as well as other gases and the absence of matter (i.e. vacuum environment). These entrapped gaps may be created utilizing any number of known techniques such as the injection of microencapsulated gaseous matter.

In a preferred embodiment, the fiber elements are formed using a continuous fiber spinning process. In this process polymer is dissolved with solvent in a highly viscous solution. The solution is dispensed through a nozzle or spinneret to form a polymer fiber. This fiber is collected by a spinning mandrel on which the stent segments are positioned. The mandrel rotates and indexes back and forth axially to cover the stent segments with polymer fiber. When the polymer fiber contacts the surface of the stent segments, it preferentially still contains enough solvent to allow for adequate solvent bonding of the fibers to each other and the surface of the metallic substrate. This process provides fibers typically in the 10 micron to 100 micron diameter range.

In another preferred embodiment, the fiber elements are formed using an electrospinning process. Herein, the polymer is typically dissolved in a solvent solution and dispensed from a spinneret and directed toward a target. A high voltage potential between the spinneret and target, in the range of 1 kV to 50 kV, creates electrostatic forces that attract the solution toward the target. Between the spinneret and mandrel, the stream of polymer in solution is transformed to a fine fiber as most of the solvent evaporates. The target is typically a rotating metallic mandrel that is either grounded or charged. Stent segments are positioned on this rotating mandrel and covered with polymer fibers using this electrostatic forming process. The mandrel may rotate at various speeds, and also index back and forth axially or spin around a carousel to achieve preferential alignment of the fibers in the axial or circumferential directions. This electrostatic spinning process typically produces fibers in a range less than one micron in diameter.

The density of the fibers may be allowed to vary from a relatively sparse network to a relatively dense network. As density increases, the device approaches the configuration of a stent graft, and may provide a barrier to flow or fluid penetration. Such an implementation with a dense mesh of biostable fibers approaches the form and function of a stent graft. However, with a dense mesh of bioabsorbable or dissolving fibers provides the functionality of a temporary stent graft; such a device may have utility in a variety of clinical circumstances, including acute repair of a vascular perforation. In a preferred embodiment, the fibers are arranged in a relatively sparse network, such that the fibers to do not provide a complete barrier to flow or fluid penetration. Such a sparse architecture is especially preferred in cases where the implanted device crosses branch vessels where it is desirable to maintain patency of such branch vessels.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. An implantable intraluminal medical scaffold comprising:
    a substantially tubular structure having first and second open ends for fluid flow therethrough and configured to maintain luminal patency of a vessel, including two or more radially expandable stent segments wherein the two or more expandable stent segments are positioned axially adjacent to each other, each of the stent segments being formed from a plurality of strut pairs;
    at least one notched tab structure located at an apex of at least one strut pair on each of the stent segments, the at least one notched tab structure having a first flat bearing surface, and
    a second flat bearing surface formed on at least two strut pairs positioned opposite the at least one notched tab on adjacent stent segments, the first flat bearing surfaces and the second flat bearing surfaces being configured to transmit compressive loads between the stent segments during deployment and
    one or more substantially axially oriented flexible fiber bridges interconnecting the adjacent two or more radially expandable stent segments to form the substantially tubular structure, the flexible fiber bridges being configured for attachment of the two or more radially expandable stent segments and arranged such that they offer substantially no impedance to fluid flow through the tubular structure, the flexible fiber bridges being anchored by a knotted loop on the at least one notched tab structure on each of the stent segments, the notched tabs being configured to hold the flexible fiber bridges.

2. The implantable intraluminal medical scaffold according to claim 1, wherein the at least one or more radially expandable stent segments comprise a balloon-expandable material.

3. The implantable intraluminal medical scaffold according to claim 2, wherein the balloon-expandable material comprises stainless steel.

4. The implantable intraluminal medical scaffold according to claim 2, wherein the balloon-expandable material comprises a cobalt-chromium alloy.

5. The implantable intraluminal medical scaffold according to claim 1, wherein the at least one or more radially expandable stent segments comprise a self-expanding material.

6. The implantable intraluminal medical scaffold according to claim 5, wherein the self-expanding material comprise a nickel-titanium alloy.

7. The implantable intraluminal medical scaffold according to claim 1, wherein the one or more flexible fiber bridges comprise individual filaments.

8. The implantable intraluminal medical scaffold according to claim 1, wherein the one or more flexible fiber bridges comprise fiber networks.

9. The implantable intraluminal medical scaffold according to claim 1, wherein the flexible fiber bridges comprise polymeric materials.

10. The implantable intraluminal medical scaffold according to claim 1, wherein the flexible fiber bridges comprise silk.

11. The implantable intraluminal medical scaffold according to claim 1, wherein the flexible fiber bridges comprise collagen.

12. The implantable intraluminal medical scaffold according to claim 1, wherein the flexible fiber bridges comprises bioabsorbable materials.

13. The implantable intraluminal medical scaffold according to claim 1, wherein the flexible fiber bridges comprise non-bioabsorbable materials.

14. The implantable intraluminal medical scaffold according to claim 1, wherein the two or more radially expandable stent segments comprise a textured surface.

15. The implantable intraluminal medical scaffold according to claim 1, wherein at least one of the two or more radially expandable stent segments and the one or more flexible fiber bridges comprise a therapeutic agent affixed thereto.

16. The implantable intraluminal medical scaffold according to claim 1, wherein at least one of the two or more radially expandable stent segments and the one or more flexible fiber bridges comprise a therapeutic agent incorporated therein.

17. The implantable intraluminal medical scaffold according to claim 1, wherein the one or more flexible fiber bridges form an interwoven network.

* * * * *